(12) United States Patent
Shetty

(10) Patent No.: US 8,575,437 B2
(45) Date of Patent: Nov. 5, 2013

(54) CUCUMBER HYBRID PS 14764212 POLL AND PARENTS THEREOF

(75) Inventor: Nischit Shetty, Ft. Myers, FL (US)

(73) Assignee: Seminis Vegetable Seeds, Inc., Woodland, CA (US)

( * ) Notice: Subject to any disclaimer, the term of this patent is extended or adjusted under 35 U.S.C. 154(b) by 220 days.

(21) Appl. No.: 13/159,343

(22) Filed: Jun. 13, 2011

(65) Prior Publication Data

US 2012/0317672 A1    Dec. 13, 2012

(51) Int. Cl.
- *A01H 5/10* (2006.01)
- *A01H 5/00* (2006.01)
- *A01H 4/00* (2006.01)

(52) U.S. Cl.
USPC ............ 800/307; 800/260; 800/265; 800/266

(58) Field of Classification Search
None
See application file for complete search history.

(56) References Cited

U.S. PATENT DOCUMENTS

2009/0265803 A1    10/2009    Shetty et al.
2011/0126309 A1    5/2011    Caldwell et al.

OTHER PUBLICATIONS

U.S. Appl. No. 61/045,551, Shetty et al.
U.S. Appl. No. 13/159,337, filed Jun. 13, 2011, Shetty.
U.S. Appl. No. 13/158,369, filed Jun. 10, 2011, Shetty.
U.S. Appl. No. 13/158,367, filed Jun. 10, 2011, Shetty.
U.S. Appl. No. 12/910,479, filed Oct. 22, 2011, Caldwell et al.
Aug. 30, 2012 Information Disclosure Statement for U.S. Appl. No. 13/159,343.

*Primary Examiner* — Brent T Page
(74) *Attorney, Agent, or Firm* — Dentons US LLP; Alissa Eagle Esq.

(57) ABSTRACT

The invention provides seed and plants of cucumber hybrid PS 14764212 POLL and the parent lines thereof. The invention thus relates to the plants, seeds and tissue cultures of cucumber hybrid PS 14764212 POLL and the parent lines thereof, and to methods for producing a cucumber plant produced by crossing such plants with themselves or with another cucumber plant, such as a plant of another genotype. The invention further relates to seeds and plants produced by such crossing. The invention further relates to parts of such plants, including the fruit and gametes of such plants.

29 Claims, No Drawings

US 8,575,437 B2

CUCUMBER HYBRID PS 14764212 POLL AND PARENTS THEREOF

FIELD OF THE INVENTION

The present invention relates to the field of plant breeding and, more specifically, to the development of cucumber hybrid PS 14764212 POLL and the inbred cucumber lines ASL 35-552 MO * HP 552 and ASL M3092040 MO.

BACKGROUND OF THE INVENTION

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

SUMMARY OF THE INVENTION

In one aspect, the present invention provides a cucumber plant of the hybrid designated PS 14764212 POLL, the cucumber line ASL 35-552 MO * HP 552 or cucumber line ASL M3092040 MO. Also provided are cucumber plants having all the physiological and morphological characteristics of such a plant. Parts of these cucumber plants are also provided, for example, including pollen, an ovule, scion, a rootstock, a fruit, and a cell of the plant.

In another aspect of the invention, a plant of cucumber hybrid PS 14764212 POLL and/or cucumber lines ASL 35-552 MO * HP 552 and ASL M3092040 MO comprising an added heritable trait is provided. The heritable trait may comprise a genetic locus that is, for example, a dominant or recessive allele. In one embodiment of the invention, a plant of cucumber hybrid PS 14764212 POLL and/or cucumber lines ASL 35-552 MO * HP 552 and ASL M3092040 MO is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

The invention also concerns the seed of cucumber hybrid PS 14764212 POLL and/or cucumber lines ASL 35-552 MO * HP 552 and ASL M3092040 MO. The cucumber seed of the invention may be provided, in particular embodiments, as an essentially homogeneous population of cucumber seed of cucumber hybrid PS 14764212 POLL and/or cucumber lines ASL 35-552 MO * HP 552 and ASL M3092040 MO. Essentially homogeneous populations of seed are generally free from substantial numbers of other seed. Therefore, seed of hybrid PS 14764212 POLL and/or cucumber lines ASL 35-552 MO * HP 552 and ASL M3092040 MO may be provided, in certain embodiments of the invention, as forming at least about 97% of the total seed, including at least about 98%, 99% or more of the seed. The seed population may be separately grown to provide an essentially homogeneous population of cucumber plants designated PS 14764212 POLL and/or cucumber lines ASL 35-552 MO * HP 552 and ASL M3092040 MO.

In yet another aspect of the invention, a tissue culture of regenerable cells of a cucumber plant of hybrid PS 14764212 POLL and/or cucumber lines ASL 35-552 MO * HP 552 and ASL M3092040 MO is provided. The tissue culture will preferably be capable of regenerating cucumber plants capable of expressing all of the physiological and morphological characteristics of the starting plant, and of regenerating plants having substantially the same genotype as the starting plant. Examples of some of the physiological and morphological characteristics of the hybrid PS 14764212 POLL and/or cucumber lines ASL 35-552 MO * HP 552 and ASL M3092040 MO include those traits set forth in the tables herein. The regenerable cells in such tissue cultures may be derived, for example, from embryos, meristems, cotyledons, pollen, leaves, anthers, roots, root tips, pistils, flowers, seed and stalks. Still further, the present invention provides cucumber plants regenerated from a tissue culture of the invention, the plants having all the physiological and morphological characteristics of hybrid PS 14764212 POLL and/or cucumber lines ASL 35-552 MO * HP 552 and ASL M3092040 MO.

In still yet another aspect of the invention, processes are provided for producing cucumber seeds, plants and fruit, which processes generally comprise crossing a first parent cucumber plant with a second parent cucumber plant, wherein at least one of the first or second parent cucumber plants is a plant of cucumber line ASL 35-552 MO * HP 552 or cucumber line ASL M3092040 MO. These processes may be further exemplified as processes for preparing hybrid cucumber seed or plants, wherein a first cucumber plant is crossed with a second cucumber plant of a different, distinct genotype to provide a hybrid that has, as one of its parents, a plant of cucumber line ASL 35-552 MO * HP 552 or cucumber line ASL M3092040 MO. In these processes, crossing will result in the production of seed. The seed production occurs regardless of whether the seed is collected or not.

In one embodiment of the invention, the first step in "crossing" comprises planting seeds of a first and second parent cucumber plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent cucumber plants into plants that bear flowers. A third step may comprise preventing self-pollination of the plants, such as by emasculating the flowers (i.e., killing or removing the pollen).

A fourth step for a hybrid cross may comprise cross-pollination between the first and second parent cucumber plants. Yet another step comprises harvesting the seeds from at least one of the parent cucumber plants. The harvested seed can be grown to produce a cucumber plant or hybrid cucumber plant.

The present invention also provides the cucumber seeds and plants produced by a process that comprises crossing a first parent cucumber plant with a second parent cucumber plant, wherein at least one of the first or second parent cucumber plants is a plant of cucumber hybrid PS 14764212 POLL and/or cucumber lines ASL 35-552 MO * HP 552 and ASL M3092040 MO. In one embodiment of the invention, cucumber seed and plants produced by the process are first generation ($F_1$) hybrid cucumber seed and plants produced by crossing a plant in accordance with the invention with another, distinct plant. The present invention further contemplates plant parts of such an $F_1$ hybrid cucumber plant, and methods of use thereof. Therefore, certain exemplary embodiments of the invention provide an $F_1$ hybrid cucumber plant and seed thereof.

In still yet another aspect, the present invention provides a method of producing a plant derived from hybrid PS 14764212 POLL and/or cucumber lines ASL 35-552 MO * HP 552 and ASL M3092040 MO, the method comprising the steps of: (a) preparing a progeny plant derived from hybrid PS 14764212 POLL and/or cucumber lines ASL 35-552 MO * HP 552 and ASL M3092040 MO, wherein said preparing comprises crossing a plant of the hybrid PS 14764212 POLL and/or cucumber lines ASL 35-552 MO * HP 552 and ASL M3092040 MO with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid PS 14764212 POLL and/or cucumber lines ASL 35-552 MO * HP 552 and ASL M3092040 MO. The plant derived from hybrid PS 14764212 POLL and/or cucumber lines ASL 35-552 MO * HP 552 and ASL M3092040 MO may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid PS 14764212 POLL and/or cucumber lines ASL 35-552 MO * HP 552 and ASL M3092040 MO is obtained which possesses some of the desirable traits of the line/hybrid as well as potentially other selected traits.

In certain embodiments, the present invention provides a method of producing food or feed comprising: (a) obtaining a plant of cucumber hybrid PS 14764212 POLL and/or cucumber lines ASL 35-552 MO * HP 552 and ASL M3092040 MO, wherein the plant has been cultivated to maturity, and (b) collecting at least one cucumber from the plant.

In still yet another aspect of the invention, the genetic complement of cucumber hybrid PS 14764212 POLL and/or cucumber lines ASL 35-552 MO * HP 552 and ASL M3092040 MO is provided. The phrase "genetic complement" is used to refer to the aggregate of nucleotide sequences, the expression of which sequences defines the phenotype of, in the present case, a cucumber plant, or a cell or tissue of that plant. A genetic complement thus represents the genetic makeup of a cell, tissue or plant, and a hybrid genetic complement represents the genetic make up of a hybrid cell, tissue or plant. The invention thus provides cucumber plant cells that have a genetic complement in accordance with the cucumber plant cells disclosed herein, and seeds and plants containing such cells.

Plant genetic complements may be assessed by genetic marker profiles, and by the expression of phenotypic traits that are characteristic of the expression of the genetic complement, e.g., isozyme typing profiles. It is understood that hybrid PS 14764212 POLL and/or cucumber lines ASL 35-552 MO * HP 552 and ASL M3092040 MO could be identified by any of the many well known techniques such as, for example, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

In still yet another aspect, the present invention provides hybrid genetic complements, as represented by cucumber plant cells, tissues, plants, and seeds, formed by the combination of a haploid genetic complement of a cucumber plant of the invention with a haploid genetic complement of a second cucumber plant, preferably, another, distinct cucumber plant. In another aspect, the present invention provides a cucumber plant regenerated from a tissue culture that comprises a hybrid genetic complement of this invention.

In still yet another aspect, the invention provides a method of determining the genotype of a plant of cucumber hybrid PS 14764212 POLL and/or cucumber lines ASL 35-552 MO * HP 552 and ASL M3092040 MO comprising detecting in the genome of the plant at least a first polymorphism. The method may, in certain embodiments, comprise detecting a plurality of polymorphisms in the genome of the plant. The method may further comprise storing the results of the step of detecting the plurality of polymorphisms on a computer readable medium. The invention further provides a computer readable medium produced by such a method.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of cucumber hybrid PS 14764212 POLL, cucumber line ASL 35-552 MO * HP 552 and cucumber line ASL M3092040 MO. The hybrid PS 14764212 POLL was produced by the cross of parent lines ASL 35-552 MO * HP 552 and ASL M3092040 MO, often with ASL M3092040 MO used as a male parent. The parent lines show uniformity and stability within the limits of environmental influence. By crossing the parent lines, uniform seed hybrid PS 14764212 POLL can be obtained.

Hybrid PS 14764212 POLL is a Monoecious Multiple Virus American Slicing cucumber for open field production. Plant habit is Indeterminate. It has higher levels of resistance to Downy mildew a fungal pathogen compared to existing hybrids in the market (Cortez). Fruits of this hybrid are dark green in color, blocky shape with blunt ends with attractive shape.

A. Origin And Breeding History Of Cucumber Hybrid PS 14764212 POLL

The hybrid PS 14764212 POLL was produced from a cross of the lines designated ASL 35-552 MO * HP 552 and ASL M3092040 MO. The parent lines are uniform and stable, as is a hybrid therefrom. A small percentage of variants can occur within commercially acceptable limits for almost any characteristic during the course of repeated multiplication. However no variants are expected.

The development of parent line ASL M3092040 MO can be summarized as follows.

Male Line ASL M3092040 MO was developed from a cross between PI 197088 Mo (98 GH2767) with ASL-2143-Mo (98 GH2714) during 1998. PI-197088 Mo is a Plant Introduction source with high levels of resistance to Downy mildew but has poor fruit quality, fruit shape, black spines and is susceptible to several virus and bacterial and fungal diseases (see Patent application for STI-DM). ASL-2143-Mo is a Monoecious Indeterminate American Slicer inbred line with good fruit quality, dark green fruit color, few spines, blocky and cylindrical shape and has resistance to Anthracnose, Angular Leaf Spot, Powdery Mildew, Scab and Cucumber Mosaic Virus. Seeds from the initial cross F1 were planted in Fall, 1998 in Woodland, Calif. and selfed to generate F2 seeds 98 GH3086-3. F2 seeds were planted in GH in 1998 in plot 4024 and selection was made based on DM resistance, plant habit, fruit shape and fruit color (98 GH4024-8). Seeds from the selection were indexed for DM in a field nursery in 1999. Seeds from selection 98 GH4024-8 were planted in the field in Felda, Fla. in 2002 during the spring season and selections were made based on yield, plant habit, fruit quality (F02S-24050E). Seeds from F02S-24050E were planted in the Fall field pollination block and selections were made for disease resistance, plant habit, fruit quality (T02F-30732B). The seeds from plot 30732B was planted in the Spring Greenhouse cycle in 2003 in plot 40700 and selections were made for fruit quality, plant habit and disease resistance (T03S-40700D). Seeds from selection 40700D was planted in the Winter Greenhouse cycle in 2004 in Tifton in plot 46516 and selections were made based on fruit quality, plant habit and disease resistance (T04W-465161), seeds from selection 465161 were planted in the greenhouse in Tifton in 2005 during the spring in plot 62682N and the line was designated as ASL M3092040 MO.

B. Physiological and Morphological Characteristics of Cucumber Hybrid PS 14764212 POLL, Cucumber Line ASL 35-552 MO * HP 552 and Cucumber Line ASL M3092040 MO In accordance with one aspect of the present invention, there is provided a plant having the physiological and morphological characteristics of cucumber hybrid PS 14764212 POLL and the parent lines thereof. A description of the physiological and morphological characteristics of such plants is presented in Tables 1-2.

TABLE 1

Physiological and Morphological Characteristics of Hybrid PS 14764212 POLL

| | Characteristic | PS 14764212 POLL | Conquistador |
|---|---|---|---|
| 1. | Type | | |
| | predominant usage | slicing/ fresh market | slicing/ fresh market |
| | predominant culture | outdoor | outdoor |
| | area of best adaptation in the USA | most areas | most areas |
| 2. | Maturity | | |
| | days from seeding to market maturity | 51 | 65 |
| 3. | Plant | | |
| | habit | vine | vine |
| | cotyledon: bitterness | present (Farbio) | present |
| | growth type | indeterminate (Corona, Levina) | indeterminate |
| | time of development of female flowers (80% of plants with at least one female flower) | early (Avir) | medium |
| | sex | monoecious (plant species in which male and female organs are found on the same plant but in different flowers - for example maize) | monoecious |
| | sex expression | monoecious when all the nodes on the plant have both male and female flowers, with more male than female flowers on each node. (Hokus) | monoecious |
| | number of female flowers per node | mostly 1 or 2 (Brunex, Marumba)) | mostly 1 |
| | flower color | orange | yellow |
| | flower color (RHS color chart value) | 14B | 14A |
| 4. | Main Stem | | |
| | main stem length | 121.3 cm | 111 cm |
| | number of nodes from cotyledon leaves to node bearing the first pistillate flower | 4.9 | 1.9 |
| | internode length | 7.4 cm | 8.1 cm |
| | stem form | grooved, ridged | grooved, ridged |
| | plant: total length of first 15 internodes | medium (Marketmore) | medium |

TABLE 1-continued

Physiological and Morphological Characteristics of Hybrid PS 14764212 POLL

| | Characteristic | PS 14764212 POLL | Conquistador |
|---|---|---|---|
| 5. | Leaf | | |
| | mature blade of third leaf: leaf length | 104 mm | 137 mm |
| | mature blade of third leaf: leaf width | 138.8 mm | 175 mm |
| | mature blade of third leaf: petiole length | 13 cm | 15.8 cm |
| | length | medium (Briljant) | medium |
| | ratio length of terminal lobe/length of blade | medium (Corona) | large |
| | shape of apex of terminal lobe | acute (Delikatess) | acute |
| | intensity of green color | medium (Rocket GS, Stereo) | dark |
| | blistering | medium (Monir) | strong |
| | undulation of margin | absent or weak (Jazzer) | moderate |
| | dentation of margin | very weak (Jazzer) | medium |
| | ovary: color of vestiture | white (Jazzer) | white |
| 7. | Fruit Set | | |
| | parthenocarpy | present (Farbio, Rocket GS, Sandra, Wilma) | absent |
| | length | long (Corona) | long |
| 6. | Fruit | | |
| | at edible maturity: fruit length | 20.1 cm | 19.3 cm |
| | diameter | small (Picobello, Wilma) | medium |
| | at edible maturity: fruit diameter at medial | 4.3 cm | 4.4 cm |
| | ratio length/diameter | large (Corona) | large |
| | core diameter in relation to diameter of fruit | small (Riesenchäl, Telepathy) | medium |
| | shape in transverse section | round to angular (Dasher) | round |
| | shape of stem end | obtuse (Maram, Score) | obtuse |
| | shape of calyx end | rounded (Bellissima) | rounded |
| | at edible maturity: fruit gram weight | 269.9 gm | 300 gm |
| | skin color/mottling | mottled or speckled with yellow | not mottled |
| | at edible maturity: yellowish blossom end stripes | absent | extended less than ⅓ of the fruit length |
| | at edible maturity: predominant color at stem end | dark green | dark green |
| | at edible maturity: Predominant color at stem end (RHS Color Chart value) | 131A | 136A |
| | at edible maturity: predominant color at blossom end | dark green | medium green |
| | at edible maturity: predominant color at blossom end (RHS Color Chart value) | 137B | 144A |
| | at edible maturity: fruit neck shape | not necked | not necked |
| | at edible maturity: fruit tapering | blossom end tapered | blossom end tapered |
| | at edible maturity: stem end cross section | circular | circular |
| | at edible maturity: medial cross section | triangular | circular |
| | at edible maturity: blossom end cross section | triangular | circular |
| | ground color of skin at market stage | yellow (Gele Tros) | green |
| | intensity of ground | medium | medium |
| | color of skin | | |
| | at edible maturity: skin thickness | thick | thin |
| | at edible maturity: skin ribs | weak (Darius, Diana) | absent |
| | sutures | present (Nabil, Silor) | absent |
| | creasing | absent (Jazzer) | absent |
| | degree of creasing | weak (Nabil) | |
| | at edible maturity: skin toughness | tender | tender |
| | at edible maturity: skin luster | dull | dull |
| | at edible maturity: spine color | white | white |
| | at edible maturity: spine quality | fine | coarse |
| | at edible maturity: spine density | few | few |
| | type of vestiture | prickles only (Corona, Jazzer) | prickles only |
| | density of vestiture | very sparse (Vert petit de Paris) | sparse |
| | density of vestiture (only varieties with white ovary vestiture) | white (Jazzer) | white |
| | warts | absent (Diana) | present |
| | at edible maturity: flavor | bitter | bitterfree |
| | length of stripes | absent or very short | short |
| | dots | present (Delicatesse, Hanpaku-Fushinari, Sagami-Fanpaku, White Sun) | present |
| | distribution of dots | in bands only (Vert petit de Paris) | predominantly in bands |
| | length of fruit containing dots | distal ⅓ | distal ⅔ |
| | density of dots | very sparse | medium |
| | glaucosity | absent or very weak (Corona) | absent or very weak |
| | length of peduncle | medium (Fendan) | medium |
| | ground color of skin at physiological ripeness | yellow | green |
| 7. | Fruit seed at harvest maturity | | |
| | measurements fruit seed length | .9 cm | .85 cm |
| | measurements fruit seed diameter at medial | .3 cm | .3 cm |
| | color | yellow | cream |
| | color RHS Color Chart value | 162D | 158C |
| | color pattern | not striped | not striped |
| | surface | smooth | smooth |
| | netting | slight or none | slight or none |
| 8. | Seeds | | |
| | number of seeds per fruit | 16.3 | 133.5 |
| | grams per 1,000 seeds | 30 gm | 26 gm |

*These are typical values. Values may vary due to environment. Other values that are substantially equivalent are also within the scope of the invention.

TABLE 2

Physiological and Morphological Characteristics of Line ASL M3092040 MO

| | Characteristic | ASL 147-M3092040 MO | Conquistador |
|---|---|---|---|
| 1. | Type | | |
| | predominant usage | slicing/ | slicing/ |

TABLE 2-continued

Physiological and Morphological Characteristics of Line ASL M3092040 MO

| Characteristic | ASL 147-M3092040 MO | Conquistador |
|---|---|---|
| predominant culture | fresh market outdoor | fresh market outdoor |
| area of best adaptation in the USA | most areas | most areas |
| 2. Maturity | | |
| days from seeding to market maturity | 64 | 65 |
| 3. Plant | | |
| habit | vine | vine |
| cotyledon: bitterness | present (Farbio) | present |
| growth type | indeterminate (Corona, Levina) | indeterminate |
| time of development of female flowers (80% of plants with at least one female flower) | early (Avir) | medium |
| sex | monoecious (plant species in which male and female organs are found on the same plant but in different flowers - for example maize) | monoecious |
| sex expression | monoecious when all the nodes on the plant have both male and female flowers, with more male than female flowers on each node. (Hokus) | monoecious |
| number of female flowers per node | mostly 1 or 2 (Brunex, Marumba) | mostly 1 |
| flower color | yellow | yellow |
| flower color (RHS color chart value) | 13B | 14A |
| 4. Main Stem | | |
| main stem length | 105.1 | 111 cm |
| number of nodes from cotyledon leaves to node bearing the first pistillate flower | 1.6 | 1.9 |
| internode length | 6.2 cm | 8.1 cm |
| stem form | grooved, ridged | grooved, ridged |
| plant: total length of first 15 internodes | medium (Marketmore) | medium |
| 5. Leaf | | |
| mature blade of third leaf: leaf length | 131.4 mm | 137 mm |
| mature blade of third leaf: leaf width | 169.3 mm | 175 mm |
| mature blade of third leaf: petiole length | 11.7 cm | 15.8 cm |
| length | medium (Briljant) | medium |
| ratio length of terminal lobe/length of blade | small (Galileo) | large |
| shape of apex of terminal lobe | acute (Delikatess) | acute |
| intensity of green color | dark (Marketmore, Sandra, Tokyo Slicer) | dark |
| blistering | weak (Pepinex 69, Rocket GS) | strong |
| undulation of margin | moderate | moderate |
| dentation of margin | weak (Hana, Silor) | medium |
| ovary: color of vestiture | white (Jazzer) | white |
| 7. Fruit Set | | |
| parthenocarpy | absent (Toska 70) | absent |
| length | long (Corona) | long |
| 6. Fruit | | |
| at edible maturity: fruit length | 22.4 cm | 19.3 cm |
| diameter | medium (Corona, Diamant) | medium |
| at edible maturity: fruit diameter at medial | 4.4 cm | 4.4 cm |
| ratio length/diameter | large (Corona) | large |
| core diameter in relation to diameter of fruit | small (Riesenchäl, Telepathy) | medium |
| shape in transverse section | round to angular (Dasher) | round |
| shape of stem end | obtuse (Maram, Score) | obtuse |
| shape of calyx end | obtuse (Reno) | rounded |
| at edible maturity: fruit gram weight | 326.8 gm | 300 gm |
| skin color/mottling | not mottled | not mottled |
| at edible maturity: yellowish blossom end stripes | extended less than ⅓ of the fruit length | extended less than ⅓ of the fruit length |
| at edible maturity: predominant color at stem end | medium green | dark green |
| at edible maturity: Predominant color at stem end (RHS Color Chart value) | 135A | 136A |
| at edible maturity: predominant color at blossom end | medium green | medium green |
| at edible maturity: predominant color at blossom end (RHS Color Chart value) | 147A | 144A |
| at edible maturity: fruit neck shape | not necked | not necked |
| at edible maturity: fruit tapering | ends blunt or rounded | blossom end tapered |
| at edible maturity: stem end cross section | circular | circular |
| at edible maturity: medial cross section | circular | circular |
| at edible maturity: blossom end cross section | circular | circular |
| ground color of skin at market stage | green (Corona) | green |
| intensity of ground color of skin | medium | medium |
| at edible maturity: skin thickness | thick | thin |
| at edible maturity: skin ribs | weak (Darius, Diana) | absent |
| sutures | present (Nabil, Silor) | absent |
| creasing | present (Corona, Nabil) | absent |
| at edible maturity: skin toughness | tender | tender |
| at edible maturity: skin luster | glossy | dull |
| at edible maturity: spine color | white | white |
| at edible maturity: spine quality | coarse | coarse |
| at edible maturity: spine density | few | few |
| type of vestiture | hairs and prickles (De Bourbonne, De Massy) | prickles only |
| density of vestiture | medium (Tasty Green) | sparse |
| density of vestiture (only varieties with white ovary vestiture) | white (Jazzer) | white |
| warts | present (Chinese Slangen, Dumex, Regal) | present |

TABLE 2-continued

Physiological and Morphological Characteristics of Line ASL M3092040 MO

| Characteristic | ASL 147-M3092040 MO | Conquistador |
|---|---|---|
| at edible maturity: tubercles (warts) | few, prominent (Salad) | few, obscure |
| size of warts | small (Jazzer) | very small |
| at edible maturity: flavor | bitter | bitterfree |
| length of stripes | short (Astrea) | short |
| dots | present (Delicatesse, Hanpaku-Fushinari, Sagami-Fanpaku, White Sun) | present |
| distribution of dots | evenly distributed (Sagami-Fanpaku) | predominantly in bands |
| length of fruit containing dots | distal ⅓ | distal ⅔ |
| density of dots | very sparse | medium |
| glaucosity | weak (Crispina, Joen-bakdadaki) | absent or very weak |
| length of peduncle | medium (Fendan) | medium |
| ground color of skin at physiological ripeness | yellow | green |
| 7. Fruit seed at harvest maturity | | |
| measurements fruit seed length | .9 cm | .85 cm |
| measurements fruit seed diameter at medial | .3 cm | .3 cm |
| color | cream | cream |
| color RHS Color Chart value | 158A | 158C |
| color pattern | not striped | not striped |
| surface | smooth | smooth |
| netting | slight or none | slight or none |
| 8. Seeds | | |
| number of seeds per fruit | 118 | 133.5 |
| grams per 1,000 seeds | 30 gm | 26 gm |

*These are typical values. Values may vary due to environment. Other values that are substantially equivalent are also within the scope of the invention.

C. Breeding Cucumber Plants

One aspect of the current invention concerns methods for producing seed of cucumber hybrid PS 14764212 POLL involving crossing cucumber lines ASL 35-552 MO * HP 552 and ASL M3092040 MO. Alternatively, in other embodiments of the invention, hybrid PS 14764212 POLL, line ASL 35-552 MO * HP 552, or line ASL M3092040 MO may be crossed with itself or with any second plant. Such methods can be used for propagation of hybrid PS 14764212 POLL and/or the cucumber lines ASL 35-552 MO * HP 552 and ASL M3092040 MO, or can be used to produce plants that are derived from hybrid PS 14764212 POLL and/or the cucumber lines ASL 35-552 MO * HP 552 and ASL M3092040 MO. Plants derived from hybrid PS 14764212 POLL and/or the cucumber lines ASL 35-552 MO * HP 552 and ASL M3092040 MO may be used, in certain embodiments, for the development of new cucumber varieties.

The development of new varieties using one or more starting varieties is well known in the art. In accordance with the invention, novel varieties may be created by crossing hybrid PS 14764212 POLL followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plants of the present invention are particularly well suited for the development of new lines based on the elite nature of the genetic background of the plants. In selecting a second plant to cross with PS 14764212 POLL and/or cucumber lines ASL 35-552 MO * HP 552 and ASL M3092040 MO for the purpose of developing novel cucumber lines, it will typically be preferred to choose those plants which either themselves exhibit one or more selected desirable characteristics or which exhibit the desired characteristic(s) when in hybrid combination. Examples of desirable traits may include, in specific embodiments, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of cucumber plants developed by this invention.

D. Performance Characteristics

As described above, hybrid PS 14764212 POLL exhibits desirable agronomic traits. The performance characteristics of hybrid PS 14764212 POLL were the subject of an objective analysis of the performance traits relative to other varieties. The results of the analysis are presented below.

TABLE 3

Performance Data for Hybrid PS 14764212 POLL

| | Average Length | Average Diameter |
|---|---|---|
| CONQUISTADOR | 7.5 | 1.7 |
| PS 14764212 POLL | 8.75 | 2 |

E. Further Embodiments of the Invention

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those cucumber plants which are developed by a plant breeding technique called backcrossing, wherein essentially all of the morphological and physiological characteristics of a variety are recovered in addition to the single locus transferred into the variety via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. The parental cucumber plant which contributes the locus for the desired characteristic is termed the nonrecurrent or donor parent. This terminology refers to the fact that the nonrecurrent parent is used one time in the backcross protocol and therefore does not recur. The parental cucumber plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (nonrecurrent parent) that carries the single locus of interest to be transferred. The resulting progeny from this cross are then crossed again to the recurrent parent and the process is repeated until a cucumber plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny cucumber plants of a backcross in which a plant described herein is the recurrent parent comprise (i) the desired trait from the non-recurrent parent and (ii) all of the physiological and morphological characteristics of cucumber the recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of cucumber plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., 1998).

F. Plants Derived by Genetic Engineering

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., 1985; Omirulleh et al., 1993; Fromm et al., 1986; Uchimiya et al., 1986; Marcotte et al., 1988). Transformation of plants and expression of foreign genetic elements is exemplified in Choi et al. (1994), and Ellul et al. (2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., 1985), including in monocots (see, e.g., Dekeyser et al., 1990; Terada and Shimamoto, 1990); a tandemly duplicated version of the CaMV $^{35}$S promoter, the enhanced $^{35}$S promoter (P-e35S); 1 the nopaline synthase promoter (An et al., 1988); the octopine synthase promoter (Fromm et al., 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a commelina yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., 1988), (2) light (e.g., pea rbcS-3A promoter, Kuhlemeier et al., 1989; maize rbcS promoter, Schaffner and Sheen, 1991; or chlorophyll a/b-binding protein promoter, Simpson et al., 1985), (3) hormones, such as abscisic acid (Marcotte et al., 1989), (4) wounding (e.g., wunI, Siebertz et al., 1989); or (5) chemicals such as methyl jasmonate, salicylic acid, or Safener. It may also be advantageous to employ organ-specific promoters (e.g., Roshal et al., 1987; Schernthaner et al., 1988; Bustos et al., 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a cucumber plant according to the invention. Non-limiting examples of particular genes and corresponding phenotypes one may choose to introduce into a cucumber plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos. 5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., 1991). The RNA could also be a catalytic RNA molecule (i.e., a ribozyme) engineered to cleave a desired endogenous mRNA product (see for example, Gibson and Shillito, 1997). Thus, any gene which produces a protein or mRNA which expresses a phenotype or morphology change of interest is useful for the practice of the present invention.

G. Definitions

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Self-pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a cucumber variety are recovered in addition to the characteristics of the single locus transferred into the variety via the backcrossing technique and/or by genetic transformation.

Substantially Equivalent: A characteristic that, when compared, does not show a statistically significant difference (e.g., $p=0.05$) from the mean.

Tissue Culture: A composition comprising isolated cells of the same or a different type or a collection of such cells organized into parts of a plant.

Transgene: A genetic locus comprising a sequence which has been introduced into the genome of a cucumber plant by transformation.

H. Deposit Information

A deposit of cucumber hybrid PS 14764212 POLL and inbred parent line ASL M3092040 MO, disclosed above and recited in the claims, has been made with the American Type Culture Collection (ATCC), 10801 University Blvd., Manassas, Va. 20110-2209. The dates of the deposits were Apr. 22, 2011 and Apr. 13, 2011, respectively. The accession numbers for those deposited seeds of cucumber hybrid PS 14764212 POLL and inbred parent line ASL M3092040 MO are ATCC Accession Number PTA-11846 and ATCC Accession Number PTA-11817, respectively. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

REFERENCES

The following references, to the extent that they provide exemplary procedural or other details supplementary to those set forth herein, are specifically incorporated herein by reference:

U.S. Pat. No. 5,378,619
U.S. Pat. No. 5,463,175
U.S. Pat. No. 5,500,365
U.S. Pat. No. 5,563,055
U.S. Pat. No. 5,633,435
U.S. Pat. No. 5,689,052
U.S. Pat. No. 5,880,275
An et al., *Plant Physiol.*, 88:547, 1988.
Bird et al., *Biotech. Gen. Engin. Rev.*, 9:207, 1991.
Bustos et al., *Plant Cell*, 1:839, 1989.
Callis et al., *Plant Physiol.*, 88:965, 1988.
Choi et al., *Plant Cell Rep.*, 13: 344-348, 1994.
Dekeyser et al., *Plant Cell*, 2:591, 1990.
Ellul et al., *Theor. Appl. Genet.*, 107:462-469, 2003.
EP 534 858
Fraley et al., *Bio/Technology*, 3:629-635, 1985.
Fromm et al., *Nature*, 312:791-793, 1986.

Fromm et al., *Plant Cell,* 1:977, 1989.
Gibson and Shillito, *Mol. Biotech.,* 7:125, 1997
Klee et al., *Bio-Technology,* 3(7):637-642, 1985.
Kuhlemeier et al., *Plant Cell,* 1:471, 1989.
Marcotte et al., *Nature,* 335:454, 1988.
Marcotte et al., *Plant Cell,* 1:969, 1989.
Odel et al., *Nature,* 313:810, 1985.
Omirulleh et al., *Plant Mol. Biol.,* 21(3):415-428, 1993.
Potrykus et al., *Mol. Gen. Genet.,* 199:183-188, 1985.
Roshal et al., *EMBO J.,* 6:1155, 1987.
Schaffner and Sheen, *Plant Cell,* 3:997, 1991.
Schernthaner et al., *EMBO J.,* 7:1249, 1988.
Siebertz et al., *Plant Cell,* 1:961, 1989.
Simpson et al., *EMBO J.,* 4:2723, 1985.
Terada and Shimamoto, *Mol. Gen. Genet.,* 220:389, 1990.
Uchimiya et al., *Mol. Gen. Genet.,* 204:204, 1986.
Wang et al., *Science,* 280:1077-1082, 1998.
Williams et al., *Nucleic Acids Res.,* 1 8:6531-6535, 1990.
WO 99/31248

What is claimed is:

1. A cucumber plant comprising at least a first set of the chromosomes of cucumber line ASL M3092040 MO, a sample of seed of said line having been deposited under ATCC Accession No. PTA-11817.

2. A seed comprising at least a first set of the chromosomes of cucumber line ASL M3092040 MO, a sample of seed of said line having been deposited under ATCC Accession No. PTA-11817.

3. The plant of claim 1, which is hybrid.

4. The plant of claim 3, wherein the hybrid plant is cucumber hybrid PS 14764212 POLL, a sample of seed of said hybrid having been deposited under ATCC Accession No. PTA-11846.

5. A plant part of the plant of claim 1.

6. The plant part of claim 5, further defined as a leaf, a ovule, pollen, a fruit, or a cell.

7. The plant part of claim 6, further defined as a fruit.

8. A cucumber plant, or a part thereof, having all the physiological and morphological characteristics of the cucumber plant of claim 1.

9. A cucumber plant, or a part thereof, having all the physiological and morphological characteristics of the cucumber plant of claim 4.

10. A tissue culture of regenerable cells of the plant of claim 1.

11. The tissue culture according to claim 10, comprising cells or protoplasts from a plant part selected from the group consisting of embryos, meristems, cotyledons, pollen, leaves, anthers, roots, root tips, pistil, flower, seed and stalks.

12. A cucumber plant regenerated from the tissue culture of claim 11.

13. A method of vegetatively propagating the plant of claim 1 comprising the steps of:
    (a) obtaining tissue capable of being propagated from a plant according to claim 1;
    (b) cultivating said tissue to obtain proliferated shoots; and
    (c) rooting said proliferated shoots to obtain rooted plantlets.

14. The method of claim 13, further comprising growing plants from said rooted plantlets.

15. A method of introducing a desired trait into a cucumber line comprising:
    (a) crossing a plant of line ASL M3092040 MO, a sample of seed of said line having been deposited under ATCC Accession No. PTA-11817, with a second cucumber plant that comprises a desired trait to produce F1 progeny;
    (b) selecting an F1 progeny that comprises the desired trait;
    (c) crossing the selected F1 progeny with a plant of line ASL M3092040 MO to produce backcross progeny; and
    (d) repeating steps (b) and (c) three or more times to produce selected fourth or higher backcross progeny that comprise the desired trait.

16. A cucumber plant produced by the method of claim 15.

17. A method of producing a plant comprising a transgene, the method comprising introducing a transgene into a plant of cucumber hybrid PS 14764212 POLL or cucumber line ASL M3092040 MO, a sample of seed of said hybrid and line having been deposited under ATCC Accession No. PTA-11846 and ATCC Accession No. PTA-11817, respectively.

18. A plant produced by the method of claim 17.

19. A plant of cucumber hybrid PS 14764212 POLL or cucumber line ASL M3092040 MO further comprising a transgene, a sample of seed of said hybrid and line having been deposited under ATCC Accession No. PTA-11846 and ATCC Accession No. PTA-11817, respectively.

20. A seed that produces the plant of claim 19.

21. A plant of cucumber hybrid PS 14764212 POLL or cucumber line ASL M3092040 MO comprising a single locus conversion, a sample of seed of said hybrid and line having been deposited under ATCC Accession No. PTA-11846 and ATCC Accession No. PTA-11817, respectively.

22. A seed that produced the plant of claim 21.

23. A method for producing a seed of a plant derived from hybrid PS 14764212 POLL or line ASL M3092040 MO comprising the steps of:
    (a) crossing a cucumber plant of hybrid PS 14764212 POLL or line ASL M3092040 MO with a second cucumber plant; a sample of seed of said hybrid and line having been deposited under ATCC Accession No. PTA-11846 and ATCC Accession No. PTA-11817, respectively; and
    (b) allowing seed of a hybrid PS 14764212 POLL or line ASL M3092040 MO-derived cucumber plant to form.

24. The method of claim 23, further comprising the steps of:
    (c) crossing a plant grown from said hybrid PS 14764212 POLL or ASL M3092040 MO-derived cucumber seed with itself or a second cucumber plant to yield additional hybrid PS 14764212 POLL or ASL M3092040 MO-derived cucumber seed;
    (d) growing said additional hybrid PS 14764212 POLL or ASL M3092040 MO-derived cucumber seed of step (c) to yield additional hybrid PS 14764212 POLL or ASL M3092040 MO-derived cucumber plants; and
    (e) repeating the crossing and growing steps of (c) and (d) to generate at least a first further hybrid PS 14764212 POLL or ASL M3092040 MO-derived cucumber plant.

25. The method of claim 23, wherein the second cucumber plant is of an inbred cucumber line.

26. The method of claim 24, further comprising:
    (f) crossing the further hybrid PS 14764212 POLL or ASL M3092040 MO-derived cucumber plant with a second cucumber plant to produce seed of a hybrid progeny plant.

27. A method of producing a cucumber comprising:
    (a) obtaining a plant according to claim 1, wherein the plant has been cultivated to maturity; and
    (b) collecting a cucumber from the plant.

28. The method of claim 27, wherein the plant is a plant of cucumber hybrid PS 14764212 POLL, a sample of seed of said hybrid PS 14764212 POLL having been deposited under ATCC Accession No. PTA-11846.

29. A method of producing seed comprising crossing the plant of claim 1 with itself or a second plant.

\* \* \* \* \*